United States Patent [19]

Wienecke

[11] Patent Number: 4,529,748

[45] Date of Patent: Jul. 16, 1985

[54] DENTAL PROSTHESIS ADHESIVE

[75] Inventor: Horst G. P. Wienecke, Gross-Gerau, Fed. Rep. of Germany

[73] Assignee: Richardson GmbH, Gross-Gerau, Fed. Rep. of Germany

[21] Appl. No.: 600,442

[22] Filed: Apr. 16, 1984

Related U.S. Application Data

[63] Continuation-in-part of Ser. No. 408,517, Aug. 16, 1982, abandoned.

[51] Int. Cl.³ .............................................. A61K 6/08
[52] U.S. Cl. .................................. 523/120; 433/168; 433/180
[58] Field of Search ................ 433/168, 180; 523/120; 106/35

[56] References Cited

U.S. PATENT DOCUMENTS 2,931,782  4/1960  Jarrett ............................. 428/407
4,271,213  6/1981  Grimm ............................ 428/407

Primary Examiner—Lorenzo B. Hayes
Attorney, Agent, or Firm—George W. Rauchfuss, Jr.; Salvatore R. Conte

[57] ABSTRACT

The invention relates to a dental prosthesis adhesive formed from one or more adhesive substances and characterized in that at least a part of the adhesive substance or substances are provided with a coating which dissolves slowly in saliva and/or ingestive liquids. Preferably the coating for the adhesive substance contains one or more film-forming substances selected from the group consisting of ethyl cellulose, saccharose monostearate, gum arabic, cellulose acetate phthalate, acrylate polymers, methacrylate polymers, shellac or other film providing substances.

16 Claims, No Drawings

DENTAL PROSTHESIS ADHESIVE

RELATED APPLICATION

This application is a continuation-in-part of earlier filed U.S. patent application Ser. No. 408,517 filed Aug. 16, 1982, now abandoned.

FIELD OF THE INVENTION

The invention relates to a dental prosthesis adhesive containing one or ore adhesive substances as well as a process for producing a dental prosthesis adhesive.

BACKGROUND OF THE INVENTION

It is generally known to produce dental prosthesis adhesives using chemical or natural substances imparting an adhesive action and which are used individually, mixed with one another or distributed in carrier substances. These dental prosthesis adhesives give a natural prosthesis fit, which generally lasts several hours.

However, in general, a maximum duration of the adhesive action is desired which should last over a maximum day-period of up to 17 or more hours. Of all known adhesives eventually one would possibly expect such a long adhesive action over the day, but it would be very difficult for the prosthesis wearer to remove the denture during the period in question whenever he would wish to do so because the adhesive action is extremely powerful. It is also extremely difficult to clean such adhesives from the dental prosthesis.

Thus, the problem of the invention is to provide a dental prosthesis adhesive permitting a reliable fit over long periods, while still making it possible to remove the prosthesis without difficulty.

SUMMARY OF THE INVENTION

According to the invention, this problem is solved in that the adhesive substance or substances are at least partly provided with a coating which slowly dissolves in the saliva and/or in ingestive liquids.

DETAILS OF THE INVENTION

The process of the invention for producing such a dental prosthesis aid is characterized by coating the adhesive substance or sustances with a coating which slowly dissolves in the salvia and/or in ingestive liquids and mixing the coated adhesive substance or substances with uncoated adhesive substance or substances.

Accordingly, the invention teaches to treat adhesive substances which ensure a reliable hold of up to 8 hours or more and which do not impair the removal of the denture in a manner providing a delaying action. Unlike the disadvantageous prior art prosthesis adhesives in which all the adhesive substances are simultaneously used in the active state, in the prosthesis adhesive according to the invention the release of the adhesion-imparting substances takes place in time-controlled manner, in that in part the adhesion-imparting substances are provided with a coating which slowly dissolves in the saliva and/or in ingestive liquids and when dissolved releases unconsumed adhesive and comes into action after the "consumption" or release or washing away of the already consumed adhesive.

The adhesive substances can be chemically defined compounds, for example sodium carboxymethyl cellulose, Karaya gum, guar gum, tragacanth, polyethylene oxide polymers; copolymers of maleic anhydride with lower alkylvinylether and mixed partial salts thereof, polyacrylamide and the like, mixtures thereof, natural substances or mixtures thereof or also mixtures with chemical substances. Optionally the denture adhesive composition may contain flavours, colorants, preservatives, fillers and other common denture adhesive additives.

The dental prosthesis adhesive according to the invention is produced by coating part of the adhesive substances with a varyingly thick protective film, and saliva or ingested liquids successively release the adhesive by dissolving the coating. The coating on the adhesive particles can be formed by the most varied film-forming substances such as e.g. ethyl cellulose, saccharose monostearate, gum arabic, cellulose acetate phthalate, acrylate polymers, methacrylate polymers, shellac and other film formers.

The coating agent, which is e.g. used as a film, can be formed by substances which are insoluble or sparingly soluble in water, their sparing solubility only occurring within specific pH ranges of from 3.5 to 9.0.

Conventionally, between approximately about 10% and 90% of the adhesive substances are coated, coating taking place e.g. by spraying adhesive substance particles with the film former dissolved in a solvent.

Conventionally, between approximately about 10% and 90% of the adhesive substances used are coated and initially the uncoated portion brings about the adhesion of the prosthesis. After washing out this uncoated portion, the remaining adhesive is slowly released after a time which can be predetermined by the choice of the coating and the thickness thereof, so that a much longer overall adhesive period can be achieved than would be possible with the uncoated adhesive. As a result of the process according to the invention, the conventional adhesion time can be extended by several additional hours. However, no difficulties are encountered if it is possibly necessary in the meantime to remove the prosthesis because the adhesion of the adhesive is always the same as with normal adhesives being effective for shorter periods.

In addition, no difficulties are encountered in cleaning the prosthesis because the conventional, easily removable prostheses adhesives can be used.

Further features and advantages of the invention can be gathered from the claims and the following description of performance examples.

EXAMPLE 1

Preparation of Adhesive Powder

About 150 kg sodium carboxymethyl cellulose (particle size max. 0.6 mm) are sprayed in a fluidized bed procedure (fluidized bed drier like AEROMATIC or GLATT) with about 120 kg of 6.5% poly [methacrylic acid, methyl methacrylate 1.2] isopropanol solution, resulting in a coating with a thickness of 2-5 micrometers. Spraying and drying are conducted in one step according to the conventional fluidized bed procedure. The yield is about 160 kg sodium carboxymethyl cellulose coated by a film.

At about 40 parts by weight of the coated sodium carboxymethyl cellulose are well mixed with about 60 parts by weight of non coated sodium carboxymethyl cellulose. The resulting pulverulent mixture can be used as an adhesive powder for dental prosthesis with a considerably longer adhesion period than conventional similar adhesives.

EXAMPLE 2

Preparation of a Semifluid Dental Prosthesis Adhesive

Twenty-four parts by weight of adhesive powder prepared in the manner described in Example 1 is incorporated into a semifluid carrier constituted by a mixture of 54 parts polyethylene glycol 400, 10 parts glycerol, 8 parts polyethylene oxide wax, 3.5 parts polyethylene glycol 6000 powder, plus a flavor premix. The resulting highly viscous liquid imparts good adhesion to a dental prosthesis for a longer period than the conventional similar adhesives.

EXAMPLE 3

Preparation of a Prosthesis Adhesive Powder

About 150 kg sodium carboxymethyl cellulose (particle size max. 0.6 mm) are sprayed in a fluidized bed procedure (fluidized bed drier like AEROMATIC or GLATT) with about 60 kg of a 6.5% ethyl alcoholic ethylcellulose solution, resulting in a coating with a thickness of 2-5 micrometer. Spraying and drying are conducted in one step according to the conventional fluidized bed procedure. The yield is about 160 kg sodium carboxymethyl cellulose, the particles thereof being coated with an ethylcellulose film.

About 50 parts by eight of the coated sodium carboxymethyl cellulose are well mixed with about 50 parts by weight of uncoated sodium carboxymethyl cellulose. The resultant powder can be used as an adhesive powder for dental prosthesis having a longer effective period than conventional similar adhesives.

EXAMPLE 4

Preparation of a Dental Prosthesis Cream

Fifty parts by weight of the adhesive powder mixture described in Example 3 is incorporated into a creamy carrier formed from 37 parts petrolatum and 12 parts liquid petrolatum. The adhesive cream provides a satisfactory adhesive action for a longer period, when applied to a dental prosthesis, than conventional similar adhesives.

Further, suitable flavorants, such as peppermint oil, or the like can be added to the denture adhesive compositions to improve the taste.

I claim:

1. In a dental prosthesis adhesive suitable for providing a reliable fit over a period of eight hours or more without impairing the ability to remove the prosthesis without undue difficulty comprising a particulate denture prosthesis adhesive, the improvement comprising a mixture of from about 10 to about 90% by weight of said adhesive particles coated with a film which dissolves slowly in saliva over said period and which is selected from the group consisting of ethyl cellulose, saccharose monostearate, gum arabic, cellulose acetate phthalate, acrylate polymers, methacrylate polymers and shellac, and the balance comprising uncoated adhesive particles.

2. In a dental prosthesis adhesive suitable for providing a reliable fit over a period of eight hours or more without impairing the ability to remove the prosthesis without undue difficulty comprising a particulate denture prosthesis adhesive selected from the group consisting of sodium carboxymethyl cellulose, karaya gum, tragacanth, polyethylene oxide polymer, copolymer of maleic anhydride with lower alkylvinyl ether and mixed partial salts thereof, polyacrylamide and mixtures thereof, the improvement comprising a mixture of from about 10 to about 90% by weight of said adhesive particles coated with a film which dissolves slowly in saliva over said period and which is selected from the group consisting of ethyl cellulose, saccharose monostearate, gum arabic, cellulose acetate phthalate, acrylate polymers, methacrylate polymers and shellac, and the balance comprising uncoated adhesive particles.

3. A dental prosthesis adhesive of claim 2 wherein the adhesive is at least partly sodium carboxymethyl cellulose.

4. A dental prosthesis adhesive of claim 2 wherein the film is sparingly soluble in water.

5. A dental prosthesis adhesive of claim 2 wherein the film is insoluble in water.

6. A dental prosthesis adhesive of claim 2 wherein the film is soluble at a pH value of from 3.5 to 9.0.

7. A dental prosthesis adhesive of claim 3 wherein the film is ethyl cellulose.

8. A dental prosthesis adhesive of claim 7 wherein 50 percent of the sodium carboxymethyl cellulose is coated with ethyl cellulose.

9. A dental prosthesis adhesive of claim 2 wherein the adhesive is incorporated in a creamy carrier formed from petrolatum and liquid petrolatum.

10. A dental prosthesis adhesive of claim 7 wherein the adhesive is incorporated in a creamy carrier formed from petrolatum and liquid petrolatum.

11. A dental prosthesis adhesive of claim 8 wherein the adhesive is incorporated in a creamy carrier formed from petrolatum and liquid petrolatum.

12. A dental prosthesis adhesive of claim 3 wherein the film is a methacrylate polymer.

13. A dental prosthesis adhesive of claim 12 wherein 40 percent of the sodium carboxymethyl cellulose is coated with a methacrylate polymer.

14. A dental prosthesis adhesive of claim 2 wherein the adhesive is incorporated in a semifluid carrier comprising a mixture of polyethylene glycol, glycerol and polyethylene oxide wax.

15. A dental prosthesis adhesive of claim 13 wherein the adhesive is incorporated in a semifluid carrier comprising a mixture of polyethylene glycol, glycerol and polyethylene oxide wax.

16. A dental prosthesis adhesive of claim 13 wherein the methacrylate polymer is a poly-methacrylic acid/methyl methacrylate.

* * * * *